United States Patent
Sumner, Jr. et al.

(10) Patent No.: US 7,132,566 B2
(45) Date of Patent: Nov. 7, 2006

(54) PROCESS FOR THE PURIFICATION OF A CRUDE CARBOXYLIC ACID SLURRY

(75) Inventors: Charles Edwan Sumner, Jr., Kingsport, TN (US); Philip Edward Gibson, Kingsport, TN (US); Robert Lin, Kingsport, TN (US); Eric Jackson Fugate, Gate City, VA (US); Ernest William Arnold, Lake Wylie, SC (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 10/667,744

(22) Filed: Sep. 22, 2003

(65) Prior Publication Data
US 2005/0065373 A1 Mar. 24, 2005

(51) Int. Cl.
C07C 51/16 (2006.01)
C07C 51/42 (2006.01)
(52) U.S. Cl. .................. 562/486; 562/416; 562/485
(58) Field of Classification Search ................. 562/416, 562/486, 485, 487
See application file for complete search history.

(56) References Cited

U.S. PATENT DOCUMENTS

| | | | |
|---|---|---|---|
| 3,170,768 A | 2/1965 | Baldwin | |
| 3,584,039 A | 6/1971 | Meyer | |
| 3,683,018 A | 8/1972 | Longland, Jr. | |
| 3,996,271 A | 12/1976 | Yokota et al. | |
| 4,158,738 A * | 6/1979 | Scott et al. | 562/416 |
| 4,201,871 A | 5/1980 | Tanouchi et al. | |
| 4,268,690 A | 5/1981 | Komatsu et al. | |
| 4,314,073 A | 2/1982 | Crooks | |
| 4,330,676 A | 5/1982 | Moxham | |
| 4,334,086 A | 6/1982 | Hanotier et al. | |
| 4,356,319 A | 10/1982 | Roffia et al. | |
| 4,357,475 A | 11/1982 | Hanotier et al. | |
| 4,447,646 A | 5/1984 | Johnson et al. | |
| 4,588,414 A | 5/1986 | Takegami et al. | |
| 4,605,763 A | 8/1986 | Kiefer et al. | |
| 4,707,274 A | 11/1987 | Donhauser et al. | |
| 4,812,233 A | 3/1989 | Coenen et al. | |
| 4,861,919 A | 8/1989 | Robbins et al. | |
| 4,939,297 A | 7/1990 | Browder et al. | |
| 5,008,450 A | 4/1991 | Yamamoto et al. | |
| 5,080,721 A | 1/1992 | Flanigan et al. | |

(Continued)

FOREIGN PATENT DOCUMENTS

DE 31 28 474 A1 6/1982

(Continued)

OTHER PUBLICATIONS

U.S. Appl. No. 10/645,737, filed Aug. 21, 2003, Sheppard et al.

(Continued)

Primary Examiner—Taylor Victor Oh
(74) Attorney, Agent, or Firm—Steven A. Owen; Bernard J. Graves, Jr.

(57) ABSTRACT

Disclosed is a process to produce a purified carboxylic acid product. The process comprises removing impurities from a crude carboxylic acid slurry in a solid-liquid displacement zone to form a slurry product. The slurry product if further treated in a staged oxidation zone and a crystallization zone to from a crystallized product. The crystallized product is further cooled in a cooling zone and subsequently filtered and dried in a filtration and drying zone. The process produces purified carboxylic acid product having good color and low impurity levels without the use of purification steps like hydrogenation.

14 Claims, 1 Drawing Sheet

U.S. PATENT DOCUMENTS

| | | | |
|---|---|---|---|
| 5,095,146 A * | 3/1992 | Zeitlin et al. ............... 562/486 |
| 5,107,874 A | 4/1992 | Flanigan et al. |
| 5,116,423 A | 5/1992 | Kokkonen et al. |
| 5,143,554 A | 9/1992 | Koyama et al. |
| 5,200,557 A | 4/1993 | Gee et al. |
| 5,359,133 A | 10/1994 | Nazimok et al. |
| 5,454,959 A | 10/1995 | Stevens |
| 5,527,957 A | 6/1996 | Hindmarsh et al. |
| 5,563,293 A | 10/1996 | Hindmarsh et al. |
| 5,583,254 A | 12/1996 | Turner et al. |
| 5,616,792 A | 4/1997 | Bartos et al. |
| 5,635,074 A | 6/1997 | Stenstrom et al. |
| 5,643,468 A | 7/1997 | Ure |
| 5,676,847 A | 10/1997 | Yamamoto et al. |
| 5,679,846 A | 10/1997 | Hindmarsh et al. |
| 5,684,187 A | 11/1997 | Ohkoshi et al. |
| 5,698,734 A | 12/1997 | Turner et al. |
| 5,712,412 A | 1/1998 | Inary et al. |
| 5,777,161 A | 7/1998 | Inary |
| 5,840,965 A | 11/1998 | Turner et al. |
| 5,840,968 A | 11/1998 | Lee et al. |
| 5,925,786 A | 7/1999 | Isayama et al. |
| 5,955,394 A | 9/1999 | Kelly |
| 6,228,215 B1 | 5/2001 | Hoffman, Jr. |
| 6,495,044 B1 | 12/2002 | Verdoes |
| 6,517,733 B1 | 2/2003 | Carlson |
| 6,797,073 B1 | 9/2004 | Teruggi et al. |
| 2003/0004372 A1 | 1/2003 | Piras et al. |
| 2004/0245176 A1 | 12/2004 | Parker et al. |
| 2004/0260052 A1 | 12/2004 | Nagao et al. |
| 2005/0087215 A1 | 4/2005 | Miyahara et al. |

FOREIGN PATENT DOCUMENTS

| | | |
|---|---|---|
| EP | 0111784 B1 | 2/1986 |
| GB | 983677 | 2/1965 |
| GB | 1152577 | 5/1969 |
| GB | 1260755 | 1/1972 |
| GB | 1 358 520 | 7/1974 |
| GB | 1388289 | 3/1975 |
| JP | 48-26740 A | 9/1973 |
| JP | 7-149690 A | 6/1995 |
| JP | 7-291896 A | 11/1995 |
| JP | 9-286758 A | 11/1997 |
| JP | 9-286759 A | 11/1997 |
| JP | 2001-139514 A | 5/2001 |
| JP | 2001-247511 | 9/2001 |
| JP | 2001-288139 | 10/2001 |
| JP | 2002-230819 A | 8/2002 |
| WO | WO 93/24440 A1 | 12/1993 |
| WO | WO 94/17892 A1 | 8/1994 |
| WO | WO 99/31038 A1 | 6/1999 |

OTHER PUBLICATIONS

U.S. Appl. No. 10/645,734, filed Aug. 21, 2003, Sheppard et al.
PCT International Search Report.
Copending U.S. Appl. No. 10/758,676 filed Jan. 15, 2004 by Parker et al.
Copending U.S. Appl. No. 10/872,248 filed Jun. 18, 2004 by Sheppard.
Copending U.S. Appl. No. 11/346,393 filed Feb. 2, 2006.
USPTO Office Action dated Nov. 30, 2004 for U.S. Appl. No. 10/645,734.
USPTO Office Action dated Apr. 21, 2004 for U.S. Appl. No. 10/645,734.
USPTO Office Action dated Apr. 22, 2003 for U.S. Appl. No. 10/315,294.
USPTO Office Action dated Dec. 10, 2004 for U.S. Appl. No. 10/645,737.
USPTO Office Action dated Apr. 19, 2004 for U.S. Appl. No. 10/645,737.

* cited by examiner

PROCESS FOR THE PURIFICATION OF A CRUDE CARBOXYLIC ACID SLURRY

FIELD OF INVENTION

The present invention relates to a process for the purification of a crude carboxylic acid slurry. More specifically, the present invention relates to a process for the purification of a crude carboxylic acid slurry by utilizing a solid-liquid displacement zone between a primary oxidation zone and a staged oxidation zone.

BACKGROUND OF THE INVENTION

Terephthalic acid is commercially produced by oxidation of paraxylene in the presence of a catalyst, such as, for example, Co, Mn, Br and a solvent. Terephthalic acid used in the production of polyester fibers, films, and resins must be further treated to remove impurities present due to the oxidation of para-xylene. Typical commercial process produce a crude terephthalic acid then dissolve the solid crude terephthalic acid in water at high temperatures and pressures, hydrogenate the resultant solution, cool and crystallize the terephthalic acid product out of solution, and separate the solid terephthalic product from the liquid as discussed in U.S. Pat. No. 3,584,039 herein incorporated by reference.

A number of processes for producing the purified terephthalic acid solid have been developed and are commercially available. Usually, the purified terephthalic acid solid is produced in a multi-step process wherein a crude terephthalic acid is produced. The crude terephthalic acid does not have sufficient quality for direct use as starting material in commercial polyethylene terephthalate(PET). Instead, the crude terephthalic acid is usually refined to purified terephthalic acid solid.

Liquid phase oxidation of p-xylene produces crude terephthalic acid. The crude terephthalic acid is dissolved in water and hydrogenated for the purpose of converting 4-carboxybenzaldehyde to p-toluic acid, which is a more water-soluble derivative, and for the purpose of converting characteristically yellow compounds to colorless derivatives. Significant 4-carboxybenzaldehyde and p-toluic acid in the final purified terephthalic acid product is particularly detrimental to polymerization processes as they may act as chain terminators during the condensation reaction between terephthalic acid and ethylene glycol in the production of PET. Typical purified terephthalic acid contains on a weight basis less than 250 parts per million (ppm) 4-carboxybenzaldehyde and less than 150 ppm p-toluic acid.

The crude terephthalic acid typically contains on a weight basis from about 800 to 7,000 parts per million (ppm) 4-carboxybenzaldehyde and about 200 to 1,500 ppm p-toluic acid as the main impurities. The crude terephthalic acid also contains lesser amounts, about 20–200 ppm range, of aromatic compounds having the structures derived from benzil, fluorenone, and/or anthraquinone, which are characteristically yellow compounds as impurities resulting from coupling side reactions occurring during oxidation of p-xylene Such a purification process typically comprises adding water to the crude terephthalic acid to form a crude terephthalic acid slurry, which is heated to dissolve the crude terephthalic acid. The crude terephthalic acid solution is then passed to a reactor zone in which the solution is contacted with hydrogen in the presence of a heterogeneous catalyst at temperatures of about 200° to about 375° C. This reduction step converts the various color causing compounds present in the crude terephthalic acid to colorless derivatives. The principal impurity, 4-carboxybenzaldehyde, is converted to p-toluic acid.

Typical crude terephthalic acid contains excessive amounts of both 4-carboxybenzaldehyde and p-toluic acid on a weight basis. Therefore, to achieve less than 250 ppmw 4-carboxybenzaldehyde and less than 150 ppmw p-toluic acid in the purified terephthalic acid requires mechanisms for purifying the crude terephthalic acid and removing the contaminants.

In many processes, colored impurities are hydrogenated to colorless derivatives and leave the process with the terephthalic acid solid product and waste water streams. However, one embodiment of this invention provides an attractive process to produce a purified carboxylic acid slurry by utilizing a solid-liquid displacement zone comprising a solid-liquid separator after oxidation of a crude carboxylic acid slurry product and prior to final filtration and drying without the use of an hydrogenation step.

SUMMARY OF THE INVENTION

In one embodiment of the invention, a process to produce the purified carboxylic acid product is provided without the use of hydrogenation of the terephthalic acid or a process separating impurities from oxidation solvent as disclosed in U.S. Pat. No. 3,584,039.

In another embodiment of this invention, a process to produce a slurry product is provided. The process comprises removing impurities from a crude carboxylic acid slurry in a solid-liquid displacement zone to form a slurry product; wherein there is a substantial absence of terephthalic acid and isophthalic acid in the crude carboxylic acid slurry.

In another embodiment of this invention, a process to produce a purified carboxylic acid product is provided. The process comprises:

(a) removing impurities from a crude carboxylic acid slurry in a solid-liquid displacement zone to form a slurry product; wherein there is a substantial absence of terephthalic acid and isophthalic acid in the crude carboxylic acid slurry;

(b) oxidizing the slurry product in a staged oxidation zone to form a staged oxidation product;

(c) crystallizing the staged oxidation product in a crystallization zone to form a crystallized product.

In another embodiment of this invention, a process to produce a purified carboxylic acid slurry is provided. The process comprises:

(a) removing in a solid-liquid displacement zone impurities from a crude carboxylic acid slurry to form a slurry product; wherein the crude carboxylic acid slurry comprises terephthalic acid, catalyst, acetic acid, and impurities that is withdrawn at a temperature between about 140° C. and about 170° C. from the oxidation of paraxylene in a primary oxidation zone; wherein there is a substantial absence of terephthalic acid and isophthalic acid in the crude carboxylic acid slurry;

(b) oxidizing the slurry product in a staged oxidation zone to form a staged oxidation product; wherein the oxidizing is conducted at a temperature between about 190° C. to about 280° C.; and wherein the oxidizing is at a higher temperature in the staged oxidation zone than in the primary oxidation zone;

(c) crystallizing the staged oxidation product in a crystallization zone to form a crystallized product;

(d) cooling the crystallized product in a cooling zone to form a cooled purified carboxylic acid slurry; and (e) filtering and optionally drying the cooled purified carboxylic slurry in a filtration and drying zone to remove a portion of the solvent from the cooled carboxylic acid slurry to produce the purified carboxylic acid product.

In yet another embodiment of this invention, a process to produce a purified carboxylic acid product is provided. The process comprises:

(a) oxidizing an aromatic feed stock in a primary oxidation zone to form a crude carboxylic acid slurry; wherein the crude carboxylic acid slurry comprises terephthalic acid; wherein the oxidizing is conducted at a temperature between about 120° C. to about 190° C.; wherein there is a substantial absence of terephthalic acid and isophthalic acid in the crude carboxylic acid slurry;

(b) removing in a solid-liquid displacement zone impurities from a crude carboxylic acid slurry to form a slurry product; wherein the crude carboxylic acid slurry comprises terephthalic acid, catalyst, acetic acid, and impurities that is withdrawn at a temperature between about 140° C. and about 170° C. from the oxidation of paraxylene in a primary oxidation zone;

(c) oxidizing the slurry product in a staged oxidation zone to form a staged oxidation product; wherein the oxidizing is conducted at a temperature between about 190° C. to about 280° C.; and wherein the oxidizing is at a higher temperature in the staged oxidation zone than in the primary oxidation zone (d) crystallizing the staged oxidation product in a crystallization zone to form a crystallized product;

(e) cooling the crystallized product in a cooling zone to form a cooled purified carboxylic acid slurry; and (f) filtering and optionally drying the cooled purified carboxylic slurry in a filtration and drying zone to remove a portion of the solvent from the cooled carboxylic acid slurry to produce the purified carboxylic acid product.

These objects, and other objects, will become more apparent to others with ordinary skill in the art after reading this disclosure.

DETAILED DESCRIPTION OF THE INVENTION

Figure 1:
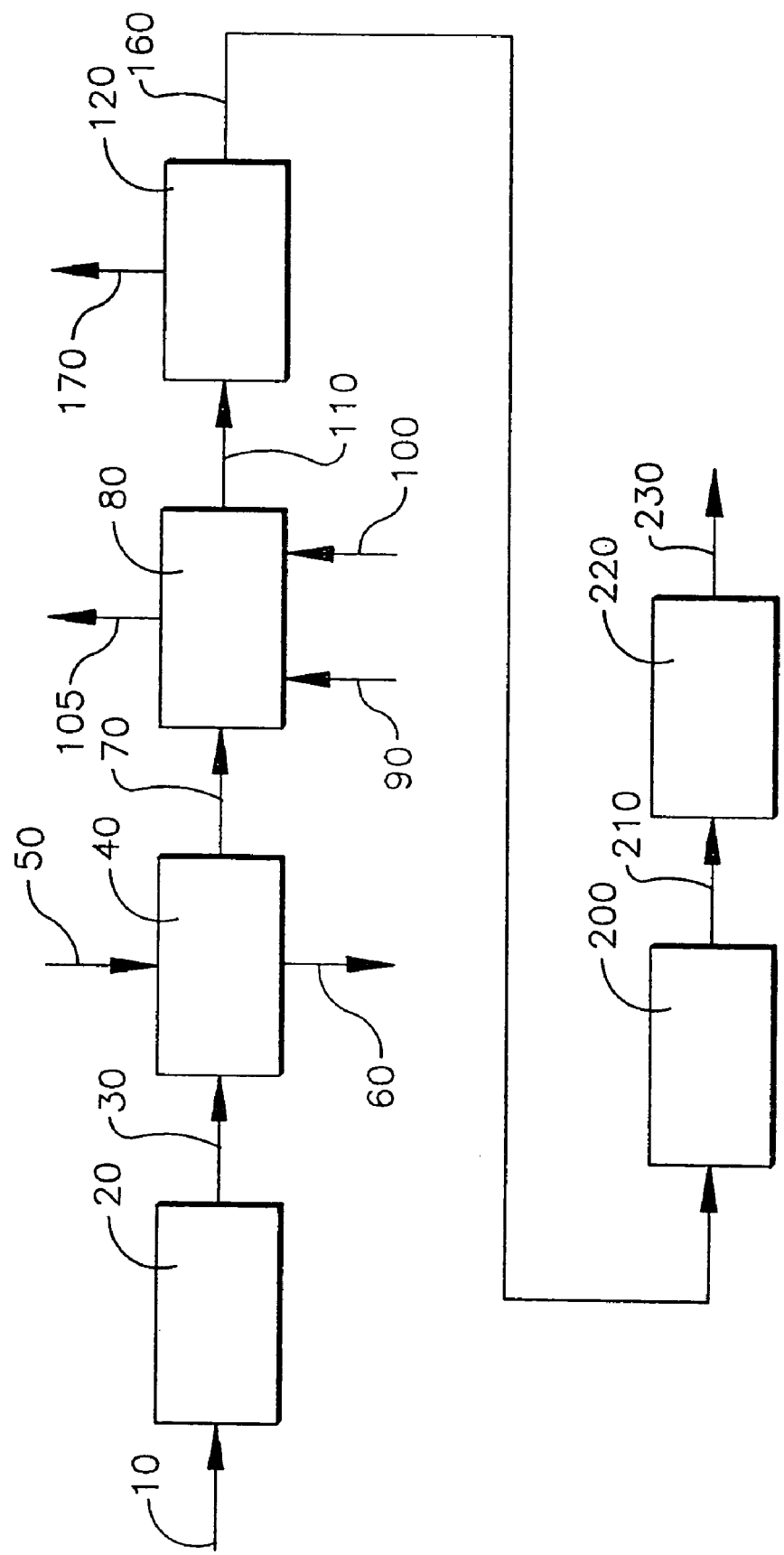
FIG. 1 is a schematic of the inventive process for the oxidative purification of carboxylic acid wherein a solid-liquid displacement zone 40 is utilized between the primary oxidation zone 20 and the staged oxidation zone 80.

The present invention provides a process for the purification of a crude carboxylic acid slurry 30. The process comprises displacing a mother liquor from the crude carboxylic acid slurry in a solid-liquid displacement zone 40 to form a slurry product 70.

Crude terephthalic acid is conventionally made via the liquid phase air oxidation of paraxylene in the presence of a suitable oxidation catalyst. Suitable catalysts comprises at least one selected from, but are not limited to, cobalt, bromine and manganese compounds, which are soluble in the selected solvent. Suitable solvents include, but are not limited to, aliphatic mono-carboxylic acids, preferably containing 2 to 6 carbon atoms, or benzoic acid and mixtures thereof and mixtures of these compounds with water. Preferably the solvent is acetic acid mixed with water, in a ratio of about 5:1 to about 25:1, preferably between about 8:1 and about 20:1. Throughout the specification acetic acid will be referred to as the solvent. However, it should be appreciated that other suitable solvents, such as those disclosed previously, may also be utilized. Patents disclosing the production of terephthalic acid such as U.S. Pat. Nos. 4,158,738 and 3,996,271 are hereby incorporated by reference.

In an embodiment of this invention, a process to produce slurry product 70 is provided in FIG. 1. The process comprises removing impurities from a crude carboxylic acid slurry 30 in a solid-liquid displacement zone 40 to form a slurry product 70; wherein the slurry product 70 is formed without a hydrogenation step.

The solid-liquid displacement zone 40, impurities, crude carboxylic acid slurry 30, and slurry product 70 are all described subsequently in this disclosure.

In another embodiment of this invention a process to produce a purified carboxylic acid product 230 is provided in FIG. 1. The process comprises:

Step (a) comprises removing impurities from a crude carboxylic acid slurry 30 in an solid-liquid displacement zone 40 to form a slurry product 70;

A crude carboxylic acid slurry 30 comprises at least one carboxylic acid, catalyst, at least one solvent, and impurities is withdrawn via line 30. The impurities typically comprise at least one or more of the following compounds: 4-carboxybenzaldehyde(4-CBA), trimellitic acid(TMA), and 2,6-dicarboxyfluorenone (2,6-DCF). The solvent typically comprises acetic acid, but can be any solvent that has been previously mentioned.

The crude carboxylic acid slurry 30 is produced by oxidizing in a primary oxidation zone 20 an aromatic feed stock 10. In one embodiment, the aromatic feedstock comprises paraxylene. The primary oxidation zone 20 comprises at least one oxidation reactor, and the crude carboxylic acid slurry 30 comprises at least one carboxylic acid. The oxidation reactor can be operated at temperatures between about 120° C. to about 200° C., preferably about 140° C. to about 170° C. Typically the aromatic feed stock 10 is paraxylene and the carboxylic acid is terephthalic acid. In one embodiment of the invention the primary oxidation zone comprises a bubble column.

Therefore, when terephthalic acid is utilized, the crude carboxylic acid slurry 30 would be referred to as crude terephthalic acid slurry and the purified carboxylic acid product 230 would be referred to as a purified terephthalic acid product.

Carboxylic acids include aromatic carboxylic acids produced via controlled oxidation of an organic substrate. Such aromatic carboxylic acids include compounds with at least one carboxylic acid group attached to a carbon atom that is part of an aromatic ring, preferably having at least 6 carbon atoms, even more preferably having only carbon atoms. Suitable examples of such aromatic rings include, but are not limited to, benzene, biphenyl, terphenyl, naphthalene, and other carbon-based fused aromatic rings. Examples of suitable carboxylic acids include, but are not limited to, terephthalic acid, benzoic acid, p-toluic, isophthalic acid, trimellitic acid, naphthalene dicarboxylic acid, and 2,5-diphenyl-terephthalic acid. Each of the embodiments of this invention can be practiced wherein there is a substantial absence of terephthalic acid and isophthalic acid in the crude carboxylic acid slurry. When the term substantial absence is used it means less than 5% by weight.

Crude terephthalic acid slurry is conventionally synthesized via the liquid phase oxidation of paraxylene in the presence of suitable oxidation catalyst. Suitable catalysts include, but are not limited to, cobalt, manganese and bromine compounds, which are soluble in the selected solvent. In one embodiment of the invention the catalyst comprises cobalt, bromine and manganese. The cobalt and manganese combined can be in concentrations of about 150 ppm to about 3200 ppm by weight in the crude carboxylic acid slurry. The bromine can be in concentrations of about 10 ppm to about 5000 ppm by weight in the crude carboxylic acid slurry. Preferably, the cobalt and manganese combined can be in concentrations of about 1050 ppm to about 2700 ppm by weight in the crude carboxylic acid slurry. The bromine can be in concentrations of about 1000 ppm to about 2500 ppm by weight in the crude carboxylic acid slurry.

The crude carboxylic acid slurry in conduit 30 is fed to a solid-liquid displacement zone 40 capable of removing a portion of the liquid contained in the crude carboxylic acid slurry 30 to produce the slurry product in conduit 70. A portion means at least 5% by weight of the liquid is removed. The removal of a portion of the liquid to produce a slurry product in conduit 70 can be accomplished by any means known in the art. Typically, the solid-liquid displacement zone 40 comprises a solid-liquid separator that is selected from the group consisting of a decanter centrifuge, rotary disk centrifuge, belt filter, rotary vacuum filter, and the like. The crude carboxylic acid slurry in conduit 30 is fed to the solid-liquid displacement zone 40 comprising a solid-liquid separator. The solid-liquid separator is operated at temperatures between about 50° C. to about 200° C., preferably 140° C. to about 170° C. The solid-liquid separator is operated at pressures between about 30 psig to about 200 psig. The solid-liquid separator in the solid-liquid displacement zone 40 may be operated in continuous or batch mode, although it will be appreciated that for commercial processes, the continuous mode is preferred.

The impurities are displaced from the solid-liquid displacement zone 40 in a mother liquor and withdrawn via line 60. In one embodiment of the invention, additional solvent is fed to the solid-liquid displacement zone 40 via line 50 to reslurry the crude carboxylic acid slurry 30 and form a slurry product 70. The mother liquor 60 is withdrawn from solid-liquid displacement zone 40 via line 60 and comprises a solvent, typically acetic acid, catalyst, and bromine compounds. The mother liquor in line 60 may either be sent to a process for separating impurities from oxidation solvent via lines not shown or recycled to the catalyst system via lines not shown. One technique for impurity removal from the mother liquor 60 commonly used in the chemical processing industry is to draw out or "purge" some portion of the recycle stream. Typically, the purge stream is simply disposed of or, if economically justified, subjected to various treatments to remove undesired impurities while recovering valuable components. Examples of impurity removal processes include U.S. Pat. No. 4,939,297 and U.S. Pat. No. 4,356,319, herein incorporated by reference.

Step (b) comprises oxidizing the slurry product 70 in a staged oxidation zone 80 to form a staged oxidation product 110.

In one embodiment of the invention, the slurry product 70 is withdrawn via line 70 to a staged oxidation zone 80 where it is heated to between about 190° C. to about 280° C. and preferably between about 200° C. to about 250° C. and further oxidized with air fed by line 100 to produce a staged oxidation product 110.

The staged oxidation zone 80 comprises at least one staged oxidation reactor vessel. The slurry product 70 is fed to the staged oxidation zone 80. The term "staged" means that the oxidation occurs in both the primary oxidation zone 20 discussed previously as well as in the staged oxidation zone 80. For example, the staged oxidation zone 80 can comprise staged oxidation reactor vessels in series.

When the carboxylic acid is terephthalic acid, the staged oxidation zone 80 comprises an oxidation reactor that is heated to between about 190° C. to about 280° C., preferably between about 200° C. to about 250° C., and most preferably between 205° C. to 225° C. and further oxidized with air or a source of molecular oxygen fed by line 100 to produce a staged oxidation product 110. Generally, oxidation in the staged oxidation zone 80 is at a higher temperature than the oxidation in the primary oxidation zone 20 to enhance the impurity removal. The staged oxidation zone 80 can be heated directly with solvent vapor, or steam via conduit 90 or indirectly by any means known in the art. Purification in the staged oxidation zone takes place by a mechanism involving recrystallization or crystal growth and oxidation of impurities.

Additional air or molecular oxygen may be fed via conduit 100 to the staged oxidation zone 80 in an amount necessary to oxidize a substantial portion of the partially oxidized products such as 4-carboxybenzaldehyde (4-CBA) in the crude carboxylic acid slurry 30 or slurry product 70 to the corresponding carboxylic acid. Generally, at least 70% by weight of the 4-CBA is converted to terephthalic acid in the staged oxidation zone 80. Preferably, at least 80% by weight of the 4-CBA is converted to terephthalic acid in the staged oxidation zone 80. Significant concentrations of 4-carboxybenzaldehyde and p-toluic acid in the terephthalic acid product are particularly detrimental to polymerization processes as they may act as chain terminators during the condensation reaction between terephthalic acid and ethylene glycol in the production of polyethylene terephthalate (PET). Typical terephthalic acid product contains on a weight basis less than about 250 parts per million (ppm) 4-carboxybenzaldehyde and less than about 150 ppm p-toluic acid Impurities in the crude carboxylic acid slurry 30 or slurry product 70 go into solution as the terephthalic acid particles are dissolved and re-crystallized in staged oxidation zone 80. Offgas from the staged oxidation zone 80 is withdrawn via line 105 and fed to a recovery system where the solvent is removed from the offgas comprising volatile organic compounds (VOCs). VOCs including methyl bromide may be treated, for example by incineration in a catalytic oxidation unit. The staged oxidation product 110 from the staged oxidation zone 80 is withdrawn via line 110.

Step (c) comprises crystallizing the staged oxidation product 110 in a crystallization zone 120 to form a crystallized product 160. Generally, the crystallization zone 120 comprises at least one crystallizer. Vapor product from the crystallization zone can be condensed in at least one condenser and returned to the crystallization zone. Optionally, the liquid from the condenser or vapor product from the crystallization zone can be recycled, or it can be withdrawn or sent to an energy recovery device. In addition, the crystallizer offgas is removed via line 170 and can be routed to a recovery system where the solvent is removed and crystallizer offgas comprising VOCs may be treated, for example by incineration in a catalytic oxidation unit.

When the carboxylic acid is terephthalic acid, the staged oxidation product 110 from the staged oxidation zone 80 is withdrawn via line 110 and fed to a crystallization zone 120 comprising at least one crystallizer where it is cooled to a temperature between about 110° C. to about 190° C. to form a crystallized product 160, preferably to a temperature between about 140° C. to about 180° C., most preferably about 150° C. to about 170° C.

The crystallized product 160 from the crystallization zone 120 is withdrawn via line 160. Typically, the crystallized product 160 is then fed directly to a vessel and cooled to form a cooled purified carboxylic acid slurry 210. When the carboxylic acid is terephthalic acid, the cooled crystallized purified carboxylic acid slurry 210 is cooled in a vessel to typically a temperature of approximately 90° C. or less before being introduced into a process for recovering the terephthalic acid as a dry powder or wet cake.

Step (d) comprises cooling the crystallized product in a cooling zone 200 to form a cooled purified carboxylic acid slurry 210.

The crystallized product 160 is withdrawn from the crystallization zone 120 via line 160. The crystallized product 160 is fed to a cooling zone 200 and cooled to less than about 90° C. to form the cooled purified carboxylic acid slurry 210. The cooling of the purified carboxylic acid slurry can be accomplished by any means known in the art, typically the cooling zone 200 comprises a flash tank.

Step (e) comprises filtering and optionally drying the cooled purified carboxylic acid slurry 210 in a filtration and drying zone 220 to remove a portion of the solvent from the cooled purified carboxylic acid slurry 210 to produce the purified carboxylic acid product 230.

The cooled, purified carboxylic acid slurry 210 is withdrawn from cooling zone 200 and fed to a filtration and drying zone 220. A portion of the solvent and remaining catalyst and impurities is separated, and the purified carboxylic acid product is withdrawn via line 230.

The filtration and drying zone 220 comprises a filter suitable for recovering the solid carboxylic acid and a dryer. The filtration can be accomplished by any means known in the art. For example, a rotary vacuum filter can be used for the filtration to produce a filtration cake. The filtration cake goes through an initial solvent removal step, is then rinsed with acid wash to remove residual catalyst, and then solvent removed again before being sent to the dryers. The drying of the filter cake can be accomplished by any means known in the art that's capable of evaporating at least 10% of the volatiles remaining in the filter cake to produce the carboxylic acid product. For example, a Single Shaft Porcupine® Processor dryer can be used.

The purified carboxylic acid product 230 has a b* less than about 4.5. Preferably, the b* color of the purified carboxylic acid product 230 is less than about 3.5. Most preferably, the b* color in purified carboxylic acid product 230 is less than about 3. The b* color is one of the three-color attributes measured on a spectroscopic reflectance-based instrument. The color can be measured by any device known in the art. A Hunter Ultrascan XE instrument in reflectance mode is typically the measuring device. Positive readings signify the degree of yellow (or absorbance of blue), while negative readings signify the degree of blue (or absorbance of yellow).

It should be appreciated that the process zones previously described can be utilized in any other logical order to produce the purified carboxylic acid product. It should also be appreciated that when the process zones are reordered that the process conditions may change.

In another embodiment of this invention each embodiment can optionally include an additional step comprising decolorizing the carboxylic acid or an esterified carboxylic acid via hydrogenation.

The decolorizing of the purified carboxylic acid slurry or an esterified carboxylic acid can be accomplished by any means known in the art and is not limited to hydrogenation. However, for example in one embodiment of the invention, the decolorizing can be accomplished by reacting a carboxylic acid that has undergone esterification treatment, for example with ethylene glycol, with molecular hydrogen in the presence of a hydrogenation catalyst in a reactor zone to produce a decolorized carboxylic acid solution or a decolorized ester product. For the reactor zone, there are no special limitations in the form or construction thereof, subject to an arrangement that allows supply of hydrogen to effect intimate contact of the carboxylic acid or ester product with the catalyst in the reactor zone. Typically, the hydrogenation catalyst is usually a single Group VIII metal or combination of Group VIII metals. Preferably, the catalyst is selected from a group consisting of palladium, ruthenium, rhodium and combination thereof. The reactor zone comprises a hydrogenation reactor that operates at a temperature and pressure sufficient to hydrogenate a portion of the characteristically yellow compounds to colorless derivatives

EXAMPLES

This invention can be further illustrated by the following example of preferred embodiments thereof, although it will be understood that these examples are included merely for purposes of illustration and are not intended to limit the scope of the invention unless otherwise specifically indicated.

EXAMPLE

Paraxylene was oxidized at 160° C. utilizing a Co, Mn, Br catalyst system to produce a crude terephthalic acid slurry having 30–35% solids. The crude terephthalic acid slurry was crystallized and purified using the process shown in FIG. 1. with the omission of a hydrogenation step and the crystallized product from the crystallization zone 120 was transferred directly to flash tank. The product was removed after filtration and drying and analyzed for 4-carboxybenzaldehyde(4-CBA), trimellitic acid(TMA), and 2,6-dicarboxyfluorenone(2,6-DCF), percent transmittance and b*. The b* is one of the three-color attributes measured on a spectroscopic reflectance-based instrument. A Hunter Ultrascan XE instrument is typically the measuring device. Positive readings signify the degree of yellow (or absorbance of blue), while negative readings signify the degree of blue (or absorbance of yellow).

The concentrations of 4-CBA, TMA, 2,6-DCF in the terephthalic acid were analyzed via liquid chromatography. To determine the percent transmittance, a 10% solution of terephthalic acid product in 2M KOH was measured using a UV visible spectrometer at 340 nm. The b* of the terephthalic acid was measured using a reflectance color method at 340 nm. The results are shown in Table 1.

| Ex. # | 4-CBA[1] (ppm) | TMA[2] (ppm) | 2,6-DCF[3] (ppm) | % T[4] | b*[5] |
|---|---|---|---|---|---|
| 1 | 103 | 51 | 10 | 89 | 4.1 |

The amount of 4-CBA present in the purified terephthalic acid product produced by the process of the present invention decreased significantly from typical levels found in the crude carboxylic acid slurry. The typical levels weren't measured during this trial but these levels were known to those skilled in the art to be about what has been previously disclosed wherein the crude carboxylic acid slurry comprising terephthalic acid, typically contains on a weight basis from about 800 to 7,000 parts per million (ppm) 4-carboxybenzaldehyde. The % transmittance of the purified terephthalic acid product has a direct influence on the color of the polyethylene terephthalate (PET) produced. Desirable PTA (purified terephthalic acid) is white (which is referred to as having low color). Higher % transmittance indicates less color in the PTA. The degree of improvement in all the measured categories is particularly surprising given the simplicity of the centrifugation in the solid-liquid separation zone and that no hydrogenation step was performed. In the past, comparable purity levels have been achieved typically by utilization of a hydrogenation plant which includes numerous steps and pieces of equipment, and significant capital investment.

The invention has been described in detail with particular reference to preferred embodiments thereof, but it will be understood that variations and modifications can be effected within the spirit and scope of the invention

We claim:

1. A process to produce a purified carboxylic acid composition comprising:
   (a) oxidizing an aromatic feed stock in a primary oxidation zone at an oxidizing temperature to form a crude carboxylic acid slurry composition; wherein said crude carboxylic acid slurry composition comprises at least one carboxylic acid; wherein there is less than 5% by weight terephthalic acid and isophthalic acid in said crude carboxylic acid slurry composition;
   (b) removing in a solid-liquid displacement zone impurities from said crude carboxylic acid slurry composition to form a slurry composition; and wherein said impurities comprise 4-carboxybenzaldehyde, trimellitic acid, or 2,6-dicarboxyfluorenone;
   (c) oxidizing said slurry composition in a staged oxidation zone to form a staged oxidation composition; wherein said oxidizing is conducted at an oxidizing temperature between about 190° C. to about 280° C.; wherein said oxidizing temperature in said staged oxidation zone is higher than the oxidizing temperature in said primary oxidation zone;
   (d) crystallizing said staged oxidation composition in a crystallization zone to form a crystallized composition;
   (e) cooling said crystallized composition in a cooling zone to form a cooled purified carboxylic acid slurry composition; and
   (f) filtering and optionally drying said cooled purified carboxylic slurry composition in a filtration and drying zone to produce said purified carboxylic acid composition.

2. The process according to claim 1 further comprising decolorizing in a reactor zone said purified carboxylic acid slurry composition or a carboxylic acid that has been esterified.

3. The process according to claim 2 wherein said decolorizing is accomplished by reacting said crude carboxylic acid slurry composition with hydrogen in the presence of a hydrogenation catalyst in said reactor zone to produce a decolorized carboxylic acid composition.

4. The process according to claim 1 wherein said solid-liquid displacement zone comprises a solid-liquid separator that is operated at a temperature between about 50° C. to about 200° C.

5. The process according to claim 1 wherein said purified carboxylic acid slurry composition has a b* of less than about 4.5.

6. The process according to claim 1 wherein said oxidizing in said primary oxidation zone is conducted in the presence of a catalyst that comprises cobalt, manganese and bromine compounds.

7. The process according to claim 6 wherein the cobalt and manganese are present in concentrations of about 1050 ppm to about 2700 ppm by weight in the crude carboxylic acid slurry composition and bromine is present at a concentration of about 1000 ppm to about 2500 ppm by weight in the crude carboxylic acid slurry composition.

8. A process to produce a purified carboxylic acid composition comprising:
   (a) oxidizing an aromatic feed stock in a primary oxidation zone at an oxidizing temperature to form a crude carboxylic acid slurry composition; wherein said crude carboxylic acid slurry composition comprises at least one carboxylic acid; wherein said oxidizing is conducted at a temperature between about 120° C. to about 200° C.; and wherein there is less than 5% by weight terephthalic acid and isophthalic acid in said crude carboxylic acid slurry composition;
   (b) removing in a solid-liquid displacement zone impurities from said crude carboxylic acid slurry composition to form a slurry composition; and wherein said impurities comprise 4-carboxybenzaldehyde, trimellitic acid, or 2,6-dicarboxyfluorenone;
   (c) oxidizing said slurry composition in a staged oxidation zone to form a staged oxidation composition; wherein said oxidizing is conducted at a temperature between about 190° C. to about 280° C.; wherein said oxidizing temperature in said staged oxidation zone is higher than the oxidizing temperature in said primary oxidation zone;
   (d) crystallizing said staged oxidation composition in a crystallization zone to form a crystallized composition;
   (e) cooling said crystallized composition in a cooling zone to form a cooled purified carboxylic acid slurry composition; and
   (f) filtering and optionally drying said cooled purified carboxylic acid slurry in a filtration and drying zone to produce said purified carboxylic acid composition.

9. The process according to claim 8 further comprising decolorizing in a reactor zone said purified carboxylic acid slurry composition or a carboxylic acid that has been esterified.

10. The process according to claim 9 wherein said decolorizing is accomplished by reacting said crude carboxylic acid slurry composition with hydrogen in the presence of a hydrogenation catalyst in said reactor zone to produce a decolorized carboxylic acid composition.

11. The process according to claim 8 wherein said solid-liquid displacement zone comprises a solid-liquid separator that is operated at a temperature between about 50° C. to about 200° C.

12. The process according to claim 8 wherein said purified carboxylic acid slurry composition has a b* of less than about 4.5.

13. The process according to claim 8 wherein said oxidizing in said primary oxidation zone is conducted in the presence of a catalyst that comprises cobalt, manganese and bromine compounds.

14. The process according to claim 13 wherein the cobalt and manganese are present in concentrations of about 1050 ppm to about 2700 ppm by weight in the crude carboxylic acid slurry composition and bromine is present at a concentration of about 1000 ppm to about 2500 ppm by weight in the crude carboxylic acid slurry composition.

* * * * *

UNITED STATES PATENT AND TRADEMARK OFFICE
CERTIFICATE OF CORRECTION

| | |
|---|---|
| PATENT NO. | : 7,132,566 B2 |
| APPLICATION NO. | : 10/667744 |
| DATED | : November 7, 2006 |
| INVENTOR(S) | : Sumner et al. |

It is certified that error appears in the above-identified patent and that said Letters Patent is hereby corrected as shown below:

Column 9, Line 64, Claim 6 "catalyst that" should read --catalyst system that--;

Column 10, Line 61, Claim 14 "and bromine" should read --and the bromine--.

Signed and Sealed this

Ninth Day of January, 2007

JON W. DUDAS
*Director of the United States Patent and Trademark Office*